United States Patent [19]

Alfano et al.

[11] Patent Number: 5,369,496
[45] Date of Patent: Nov. 29, 1994

[54] NONINVASIVE METHOD AND APPARATUS FOR CHARACTERIZING BIOLOGICAL MATERIALS

[75] Inventors: Robert R. Alfano, Bronx, N.Y.; Kwong M. Yoo, Kuala Lumpur, Malaysia; Guichen Tang, Shanghai, China

[73] Assignee: Research Foundation of City College of New York, New York, N.Y.

[21] Appl. No.: 434,799

[22] Filed: Nov. 13, 1989

[51] Int. Cl.⁵ .................................... G01N 21/47
[52] U.S. Cl. ........................ 356/446; 356/318; 356/448; 128/665
[58] Field of Search ..................... 356/445–448, 356/335–343, 73, 73.1, 317, 318, 417, 432; 128/665, 664, 672, 773, 661.03; 250/213 VT; 372/25

[56] References Cited

U.S. PATENT DOCUMENTS

| | | | |
|---|---|---|---|
| 3,782,827 | 1/1974 | Nisenson et al. | 356/447 |
| 4,178,917 | 12/1979 | Shapiro | 356/327 |
| 4,479,499 | 10/1984 | Alfano | 356/317 |
| 4,505,583 | 3/1985 | Konomi | 356/417 |
| 4,515,476 | 5/1985 | Ingmar | 356/417 |
| 4,570,638 | 2/1986 | Stoddart et al. | 128/665 |
| 4,630,925 | 12/1986 | Schiller et al. | 356/318 |
| 4,650,336 | 3/1987 | Moll | 356/417 |
| 4,695,529 | 6/1987 | Kushida | 356/317 |
| 4,718,417 | 1/1988 | Littrell et al. | 128/398 |
| 4,767,207 | 8/1988 | Takiguchi | 356/73.1 |
| 4,850,707 | 7/1989 | Bowen et al. | 356/336 |
| 4,920,386 | 4/1990 | Tsuchiya et al. | 250/213 VT |

Primary Examiner—Richard A. Rosenberger
Assistant Examiner—Hoa Q. Pham
Attorney, Agent, or Firm—Kriegsman & Kriegsman

[57] ABSTRACT

Biological material is characterized by illuminating the material with a beam of light, measuring light scattered from the material and then determining the condition of the material using the measurements. In one embodiment the angular line shape of the backscattered light is measured and then used to determine the scattering mean free path (1) and the absorption length (la) of the light scattered in the material to find out the condition of the material. These values so obtained are compared to values for a material whose condition is normal to determine if the condition of the material being examined is abnormal or normal. In another embodiment the temporal profile of the scattered pulse is used to determine (1) and (1a). The apparatus includes a laser for illuminating a section of material to be characterized, a streak camera for detecting light scattered from the material, a video camera for imaging the output of the streak camera, a computer for processing the output of the video camera to determine (1) and (1a) and a monitor for displaying the results to determine if the condition of the material being examined is normal or abnormal.

11 Claims, 17 Drawing Sheets

NONINVASIVE METHOD AND APPARATUS FOR CHARACTERIZING BIOLOGICAL MATERIALS

This invention was made with Government support under Contract N00014-87-K-0431 awarded by the Department of the Navy. The Government has certain rights in this invention.

BACKGROUND OF THE INVENTION

The present invention is related generally to a noninvasive method and apparatus for characterizing biological materials and more particularly to a noninvasive method and apparatus for characterizing the state of biological materials in humans, animals and plants using scattered light. Examples of biological materials are bones and tissues in various parts and organs of the body of humans and animals including, the breasts, the eye, the lung, the heart, arteries and teeth and leafs of plants.

It is known to use spectrum information of scattered light as a means for detecting caries. In U.S. Pat. No. 4,479,499 to R. R. Alfano there is disclosed a method for detecting the presence of caries in the teeth of a person, the method involving radiating a region of the teeth to be examined with light; producing first and second signals corresponding to the intensity of the light scattered at first and second wavelength, respectively, the intensity of difference of the scattered light between caries and non-carious regions at said first wavelength being measurably different than the intensity difference of the scattered light between caries and non-carious regions at said second wavelength producing a third signal corresponding to the difference between said first and second signal; determining the value of said third signal when a known non-carious region is radiated; and detecting the presence of caries in other regions by said third signal changing from said value in a predetermined manner.

In U.S. Pat. No. 4,718,417 to Kittrell et al there is disclosed a method of distinguishing artery wall from atheromateous plaque which involves measuring the intensity of the fluorescence irradiated from the material over a plurality of wavelengths when excited by light.

The following publications are considered pertinent to this invention.

Y. Kuga and A. Ishimaru, J. Opt. Soc. Am. A8, 831 (1984); M. P. Van Albada and Ad Lagendijk, Phys. Rev. Lett. 55, 2692 (1985); P. E. Wolf and G. Maret, Phys. Rev. Lett. 55, 2696 (1985); E. Akkermans, P. E. Wolf and R. Maynard, Phys. Rev. Lett. 56 1471 (1986); M. J. Stephen and G. Cwilich, Phys. Rev. B 34, 7564 (1986); P. E. Wolf, G. Maret, E. Akkermans, and R. Maynard, J. Phys. France 49, 63 (1988); S. Etemad, R. Thompson, M. J. Andrejco, Sajeev John and F. C. Mackintosh, Phys. Rev. Lett. 59, 1420 (1987); S. Etemad, R. Thompson, and J. J. Andrejco, Phys. Rev. Lett. 57, 1420 (1986); M. Rosenbluh, I. Edrei, M. Kaveh and I. Freud, Phys. Rev. A, 4458 (1987); M. P. van Albada, M. B. vander Mark, and Ad Lagendijk, Phys. Rev. Lett. 58,361 (1987); K. M. Yoo, Y. Takiguchi and R. R. Alfano, IEEE Photonics Tech. Lett., April 1989; K. M. Yoo, K. Arya, G. C. Tnag, J. B. Birmann, R. R. Alfano, Phys. Rev. A, 1989; M. Abramowitz, and I. A. Stegan, Handbook of Mathematical Functions, Dover (1960), Pg. 686.

It is an object of this invention to provide a new and improved method and apparatus for characterizing the state of biological materials in humans animals and plants.

It is another object of this invention to provide a method and apparatus as described above which is noninvasive.

It is yet still a further object of this invention to provide a method and apparatus as described above which involves the use of scattered light in angular and time regimes.

It is another object of this invention to provide a method and apparatus for characterizing the state of materials using backscattered light.

It is a further object of this invention to provide a method and apparatus as described above which involves the use of scattered light.

It is still a further object of this invention to provide a new and improved method and apparatus for measuring the scattering mean free path (1) and the absorption length (1a) of light scattering in random materials.

SUMMARY OF THE INVENTION

The present invention makes use of the discovery that light scattered in biological materials exhibits the phenomena of weak localization and that the transport mean free path and the absorption length of the light in such materials can be determined either from the line shape of the coherent peak or the temporal profile of the scattered pulse.

A noninvasive method of characterizing tissue according to this invention comprises illuminating the material with a beam of light, measuring light scattered from the material and then determining the condition of the tissue using the measurements. In one embodiment of the invention the angular line shape of the light scattered in the backward direction is measured and then used to determine the transport scattering mean free path (1) and the absorption length (1a) of the light scattered in the material. As is known, the transport scattering mean free path (1) is the mean distance over which the light travels between scattering and the absorption length (1a) is the distance over which the light propagates in the medium before it is absorbed. The values so obtained are compared to values for a known tissue to determine the condition of the material being examined to determine if the material is normal or abnormal. In another embodiment of the invention, the temporal profile of a scattered pulse (i.e. light scattered from a pulse illuminating the material) is used to determine (1) and (1a) from the profile.

An apparatus for characterizing biological material according to one embodiment of this invention comprises means for illuminating a section of tissue to be characterized, a streak camera for detecting light scattered from the tissue, a video camera for imaging the output of the streak camera, a computer for processing the output of the video camera and display means for displaying the results.

Various features and advantages will appear from the description to follow. In the description, reference is made to the accompanying drawing which forms a part thereof, and in which is shown by way of illustration, specific embodiments for practicing the invention. These embodiment will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

Figure 1:
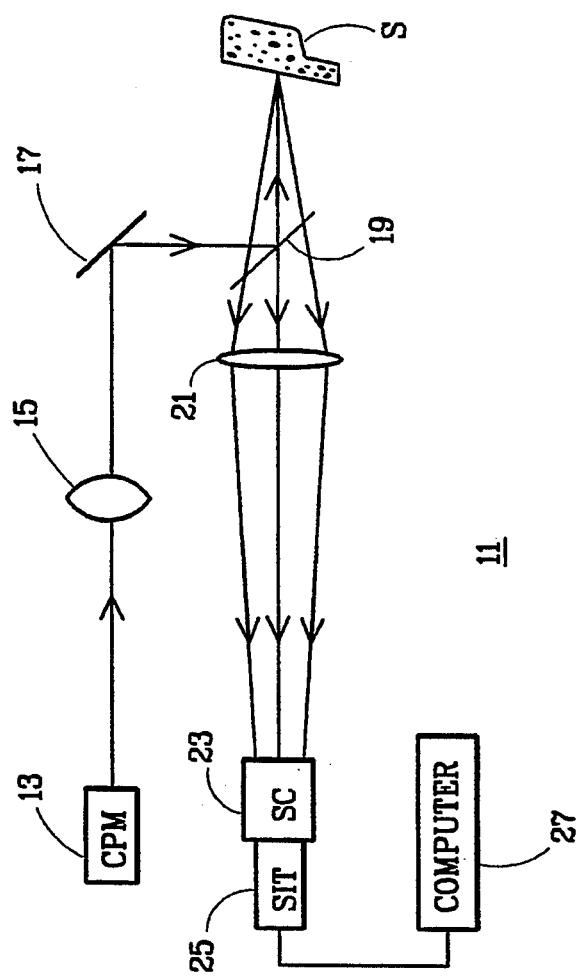
FIG. 1 is a schematic of an experimental setup used to demonstrate the method of the invention.
Figure 2:
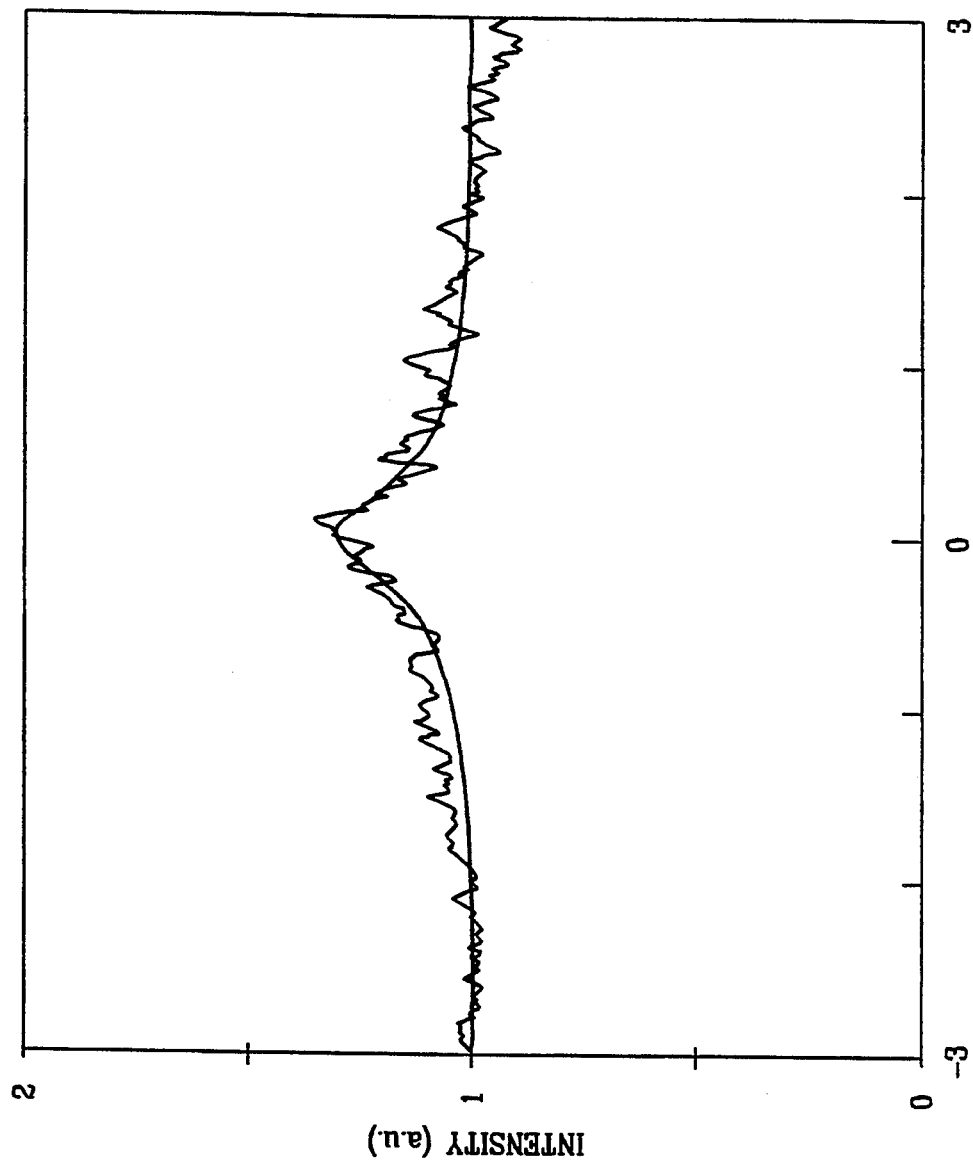
FIG. 2 is a graph of the angular distribution of intensity of light backscattered from human normal breast tissue.
Figure 3:
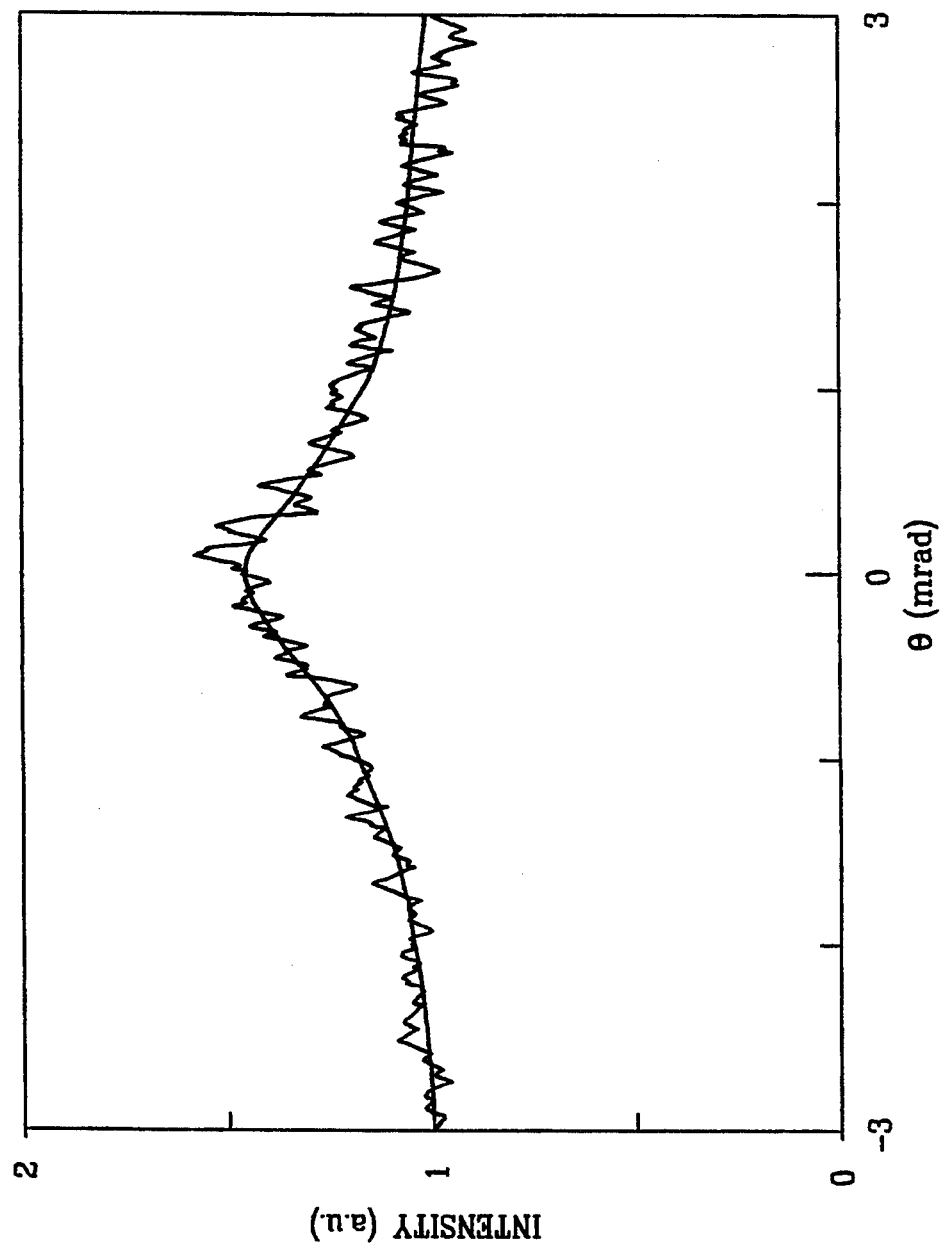
FIG. 3 is a graph of the angular distribution of intensity of light backscattered from human lung tissue.

In the field of medical and biological diagnosis, normal, benign, abnormal, cancerous or diseased materials differ from one another, either in the chemical composition or the size or the shape of the cells or parts making up the material. The chemical composition and size of the cell or part determines the transport mean free path (1) and the absorption length (1a) of light scattered in the material. In turn, l and la determine the state of goodness of the material, separating the normal from the abnormal material in early stages of development.

The present invention is based on the discovery that light scattered from biological material exhibits the phenomena of weak localization and intensity is enhanced about the backward direction. The present invention is also based on the discovery that by using the line shape of light scattered in the backward direction or the temporal profile of the scattered pulse, which is different for various states of tissue, one can characterize material.

The profile of the enhanced intensity of the scattered light from a medium about the backward direction, known as the coherent peak, depends on the transport mean free path l and the absorption length la of the light transport in the medium. The angular width of the coherent peak can be directly related to l by $$\frac{\lambda}{2\pi l},$$

where $\lambda$ is the wavelength. The angular line shape of the coherent peak can be quantitatively described by the equation:

$$\alpha(\theta) = \frac{3}{16\pi}\left[1 + 2\frac{z_0}{l} + \frac{1}{(1+ql)^2}(1 + 1 - e^{\frac{-2qQ_0}{ql}})\right] \quad (1)$$

where l is the transport mean free path, i.e. the mean distance the the photon travels between scattering, $\alpha\Theta$ is the intensity of the backscattered light as a function of angle and $\pi=3.14159$ is the angle of the scattered light measured from the exact backward direction, $$q = \frac{2\pi\theta}{\lambda}$$

for a non-absorbing media and $$\left[\left(\frac{2\pi\theta}{\lambda}\right)^2 + q_a^2\right]^{\frac{1}{2}}$$

for an absorbing media and $Z_0$ is determined by the boundary condition, in a plane interface $Z_0=0.7\ l$ where la=the absorption length of the medium i.e. the mean distance the light travels before it is absorbed in the medium. In the case of an absorbing medium, the light which undergoes long scattering path in the medium will be cut off. The intensity of the coherent peak will be reduced and the shape of the coherent peak becoming more rounded. In the absorbing media, q should be replaced by $q^1$ which is related by the equation:

$$q^1 = [q^2 + q_a^2]^{\frac{1}{2}} \quad (2)$$

where $$q_a^2 = 3/(l_a l) \quad (3)$$

The above description of coherent backscattering have been applied well for the discrete random medium. On the other hand, tissues are continuous random media which differ somewhat from the discrete random media. However, the scattering characteristics of both media can be described by the mean free path and the absorption length. Thus, one should expect the equations (1) to (3) to hold for light scattered for biological tissues.

The angular line shape of the coherent peak described in equation (1) is the sum over all the contributions from different scattering pathlength of the light inside the media. The scattered light from the short pathlength contribute to the broader coherent peak whereas those undergo long scattering pathlengths contribute to the narrower coherent peak. This will be shown in the time-resolved data later. The peak of the profile depends on la. The more absorbing media has a decrease in the size of the peak in comparison to the background.

Theoretically, the intensity of the scattered light in time domain in the direction $\hat{s}$ is $$I(\hat{s},t) = \int dt' R(\hat{s},t^1) I_o(t-t^1) \quad (4)$$

where I(s,t) is the intensity of the scattered light in the direction s at time t, s is the unit direction vector, t is time, $I_o(t-t^1)$ is the intensity of the incidence pulse as a function of time, t is the integration parameter time and $R(s,t^1)$ is defined in equation (5) below, and $R(s,t^1)$ is the response function of the random medium. In the diffusion approximation, one can write the equation:

$$R(\hat{S},t^1) = \alpha \frac{1}{\sqrt{2\pi}} e^{D_o t/2l^2} D_{-3}\left(2D_o \frac{t^1}{l^2}\right) \quad (5)$$

where $\alpha$ is some constant, l is the transport mean free path, $D_{-3}$ is the parabolic cylinder (Weber) function, $D_o = cl/3$ is the diffusion constant, and c is the effective speed of the wave in the medium. Theoretically, it corresponds to the sum of ladder diagrams in the calculation of 2-photon Green function. To include coherent interference due to time reversal symmetry in the scattering process, one should take the maximal crossed-diagrams into account. The sum of the maximal crossed-diagrams will result in a factor of $e^{-D_o q^2 t'}$ in equation (5), where $$q = \frac{2\pi}{\lambda} \sin\theta,$$

and $\Theta$ is the angle $\hat{s}$ made with the backward direction of the incident light. This term accounts for the coherent interference between scattered waves propagating in the time reversed path in the random medium, and exhibits the following important characteristics. The intensity at $\Theta = 0$ is highest and is a factor two greater than the diffusive intensity ($\Theta = 0$ corresponds to the exact backward direction); The expression for the intensity of the scattered pulse is:

$$I(\hat{S},t) = \alpha \frac{1}{\sqrt{2\pi}} \int dt' R(\hat{S},t^1)(1 + e^{-D_o q^2 t^1}) I(t-t^1) \quad (6)$$

If the random medium is absorbing, then an absorption factor of $$e^{-\frac{Ct}{l_a}}$$

should be included in the integrand of equation (6). Because of the finite temporal resolution of the detecting instrument with response function r(t−t), the measured scattered pulse profile is written as $$I_m(\hat{s},t) = \int dt' r(t-t^1) I(\hat{s},t^1) \quad (7)$$

where $I_m$ (s,t) is the measured backscattered pulse and $r(t-t_1)$ is the response time of the detecting instrument.

The schematic diagram of an experimental setup 11 is used to demonstrate the method of the invention is shown in FIG. (1). Ultrafast laser pulses were generated from colliding mode-locked dye laser 13 with wavelength center at 620 nm and bandwidth of 18 nm. The temporal pulse width of the laser was about 100 fs. The laser beam was collimated by a lens 15, deflected off a mirror 17 and incident on the biological tissues after reflection from a beam splitter 19. The tissue being studied were human normal and cancer breast and lung tissues. The scattered light was collected by a lens 21 of 500 mm focal length. A detector 23 (a streak camera) was placed at the focal plane of the lens. Each position on the face of the detector corresponded to a given scattering angle. The temporal and angular information of the scattered pulses from the tissue were acquired simultaneously. The temporal resolution of the streak camera was 10 ps and the angular resolution was 0.4 mrad. Each data was collected over a time duration of 15s. The data collected were ensemble averaged over large number of configurations by shaking the sample while the data was taken. The polarization of detection was in parallel geometry. When the tissues were held steady (no shaking) a large fluctuation of scattered intensity was observed. This large fluctuation is due to interference of the laser scattered from the random media. The output of detector 23 was imaged by an SIT video camera 25 whose output was fed into a computer 27.

FIG. (2) shows the angular distribution of the light backscattered from a sample of human normal breast tissue using the system in FIG. 1. The coherent peak is clearly seen. The theoretical fit using eqs. (1) to (3) to the experimental result give the mean free path of $250 \pm 30$ μm, and the absorption length of $4000 \pm 1000$ μm. Similar effect but with wider coherent peak was observed in a sample of human benign lung tissue which is shown in FIG. (3). A theoretical fit shows that the transport mean free path is $80 \pm 20$ μm and the absorption length is $3000 \pm 1000$ μm. This shows that the lung tissue scattered light stronger than that of breast tissue.

Figure 4:
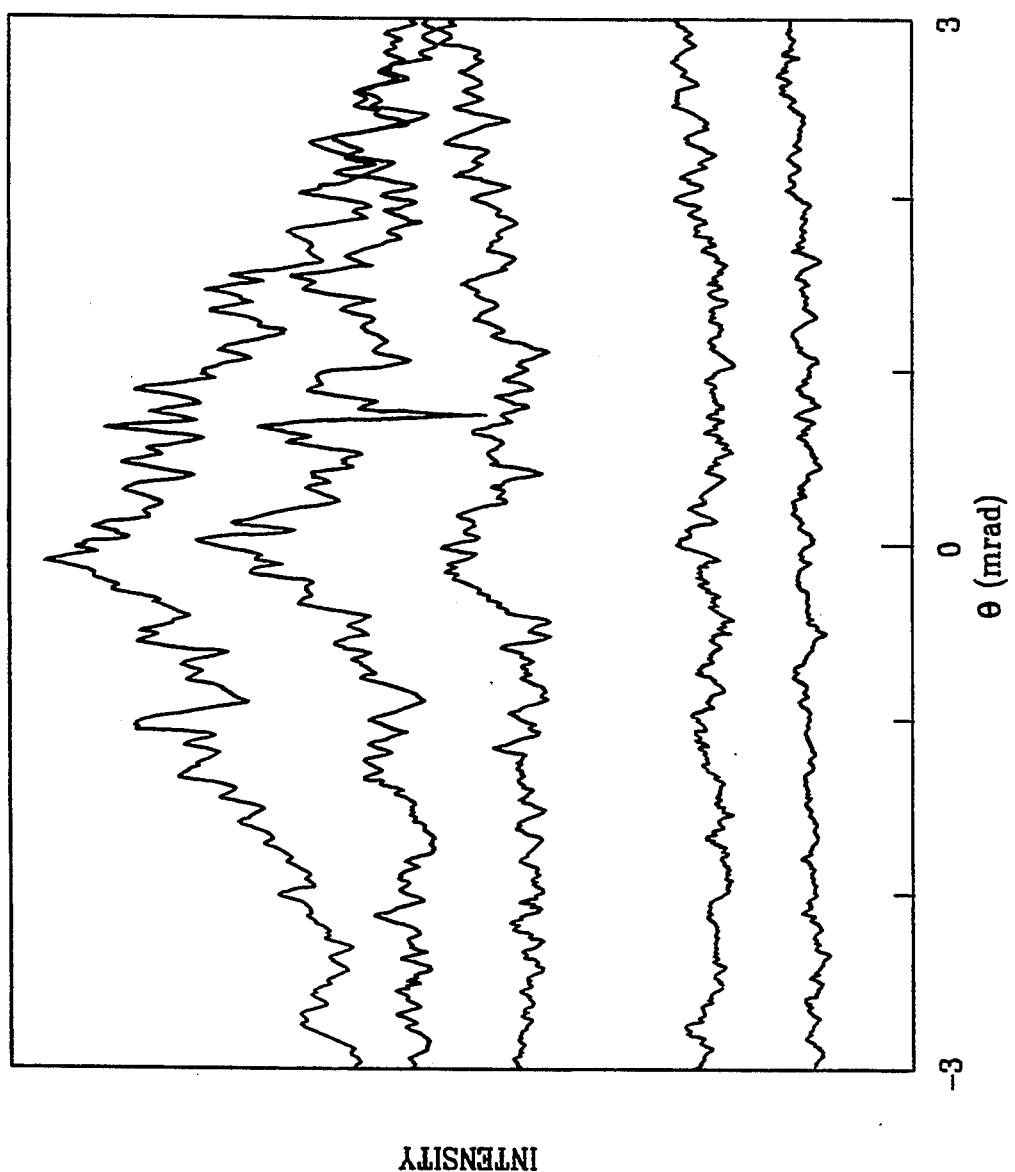
FIG. 4 is a graph showing the intensity and the line shape of the coherent peak of the scattered light at various times after an 100 fs pulse incident on lung cancer tissue. The times for the curves from the top are: 4, 8, 13, 22 and 35 ps.

The intensity and the line shape of the coherent peak of the scattered light at various times after the incident pulse is presented in FIG. 4. The sample was a cancerous lung tissue. This figure shows that the coherent peak became narrower as the light scattered through longer distances in the random media. The finite angular resolution of the streak camera reduced the intensity of the coherent peak. The coherent peak disappeared at time greater than 22 ps, due to angular resolution of the streak camera which could not detect narrower peak below 0.4 mrad.

Figure 5:
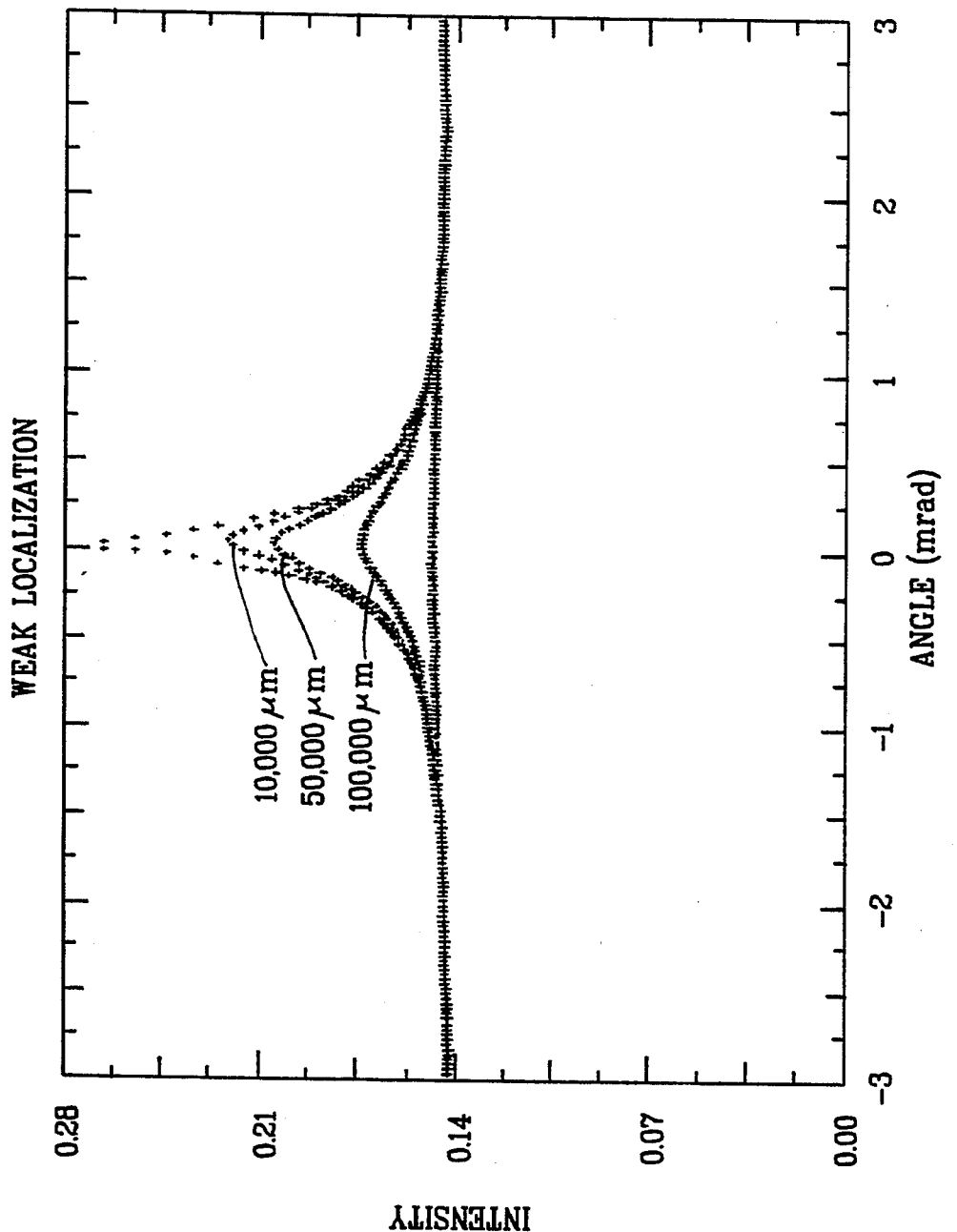
FIG. 5 is a graph showing theoretical plots of the line shape of the coherent peaks for a transport mean free path $l=250$ μm with absorption lengths of 10,000 μm, 50,000 μm and 1,000,000 μm as indicated on the curves.

The line shape of the coherent peak can be used to determine the absorption length (or absorption coefficient) of the media. Theoretical plots in FIG. 5 show the effect of absorption on the line shape of the coherent peak. The transport mean free path is 250 μm. Medium with long absorption length show a sharp coherent peak. This is due to the coherent interference of scattered light which has undergone long scattering paths and which contributes to the narrower portion of the coherent peak. As the absorption length of the medium decreases the sharp component of the coherent peak diminishes because light undergoing long scattering paths were cut off by absorption. In a strongly absorbing medium, la=100 um and hardly any coherent peak is observed.

Figure 6:
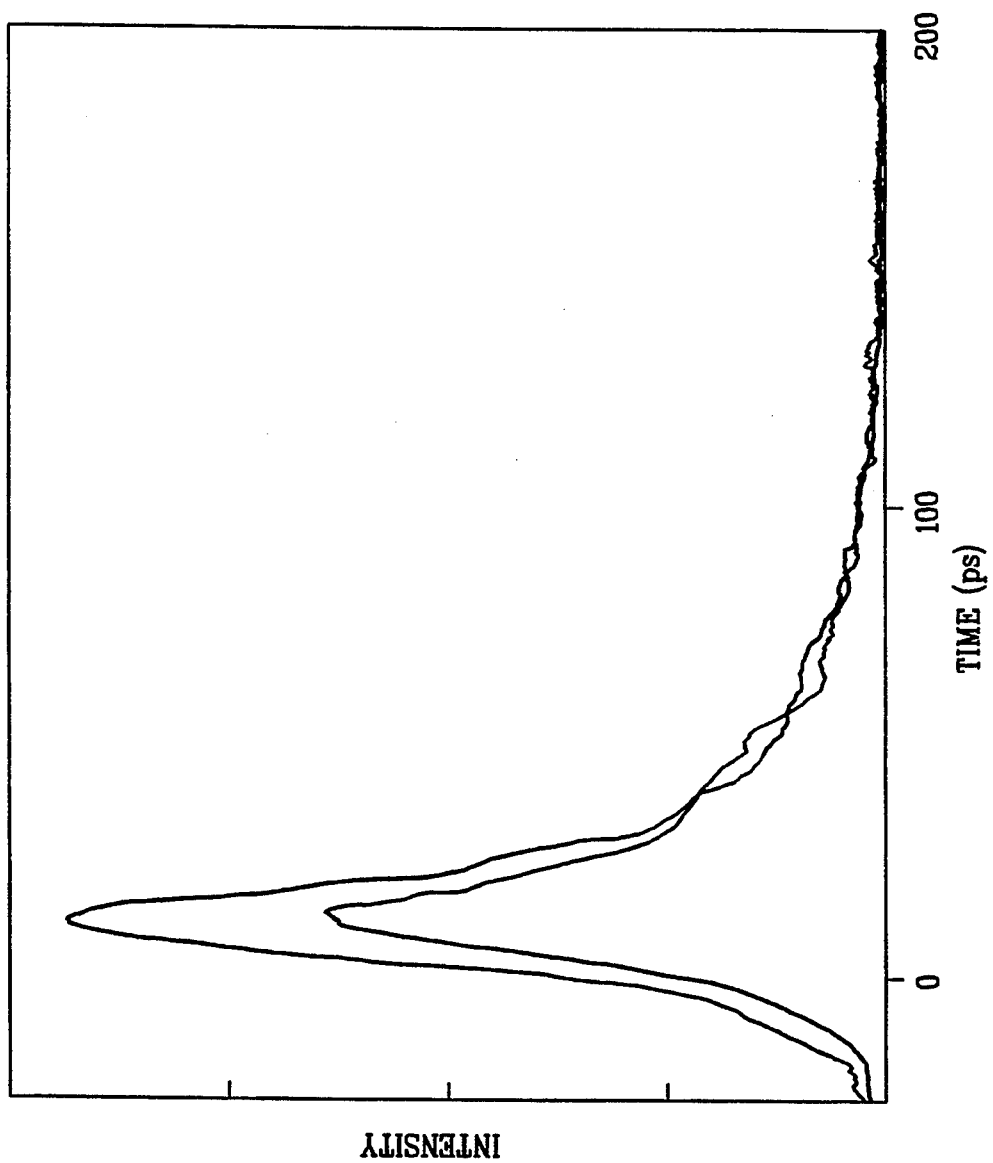
FIG. 6 is a graph showing temporal profiles of the scattered pulse from cancerous breast tissue. The higher curve is for light scattered at 0 mrad and the lower one is at 3 mrad.
Figure 7:
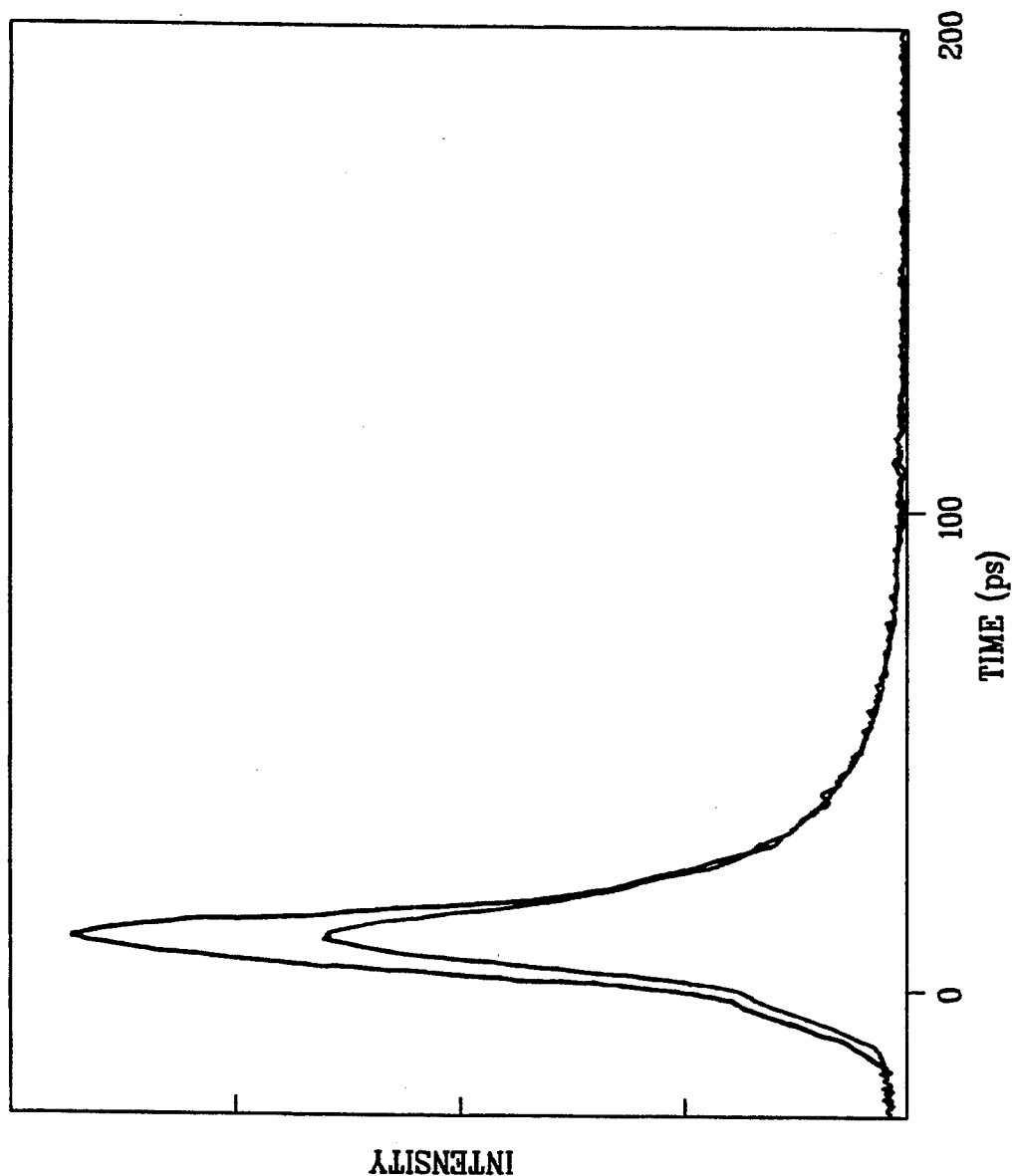
FIG. 7 is a graph showing temporal profiles of the scattered pulse from cancerous lung cancer tissue. The higher curve is for light scattered at 0 mrad and the lower is at 3 mrad.

The temporal profiles of the scattered pulse at two angular regions, coherent (at 0 mrad) and diffuse (at 3 mrad) region, for breast and lung tissues are displayed in FIGS. 6 and 7, respectively. The intensity of the scattered light in the coherent region is greater than that in the diffuse region in the early time, and they merge together at some later time. The scattered pulse from the breast cancer tissue (FIG. 6) is broader than that from the lung cancer tissue (FIG. 7). This shows that the transport mean free path of the light is longer in the breast tissue. This is in agreement with the results obtained from the line shape of the coherent peak. The mean free path and the absorption length of the light in the tissue can be obtained by fitting the temporal profile of the scattered light.

Figure 8:
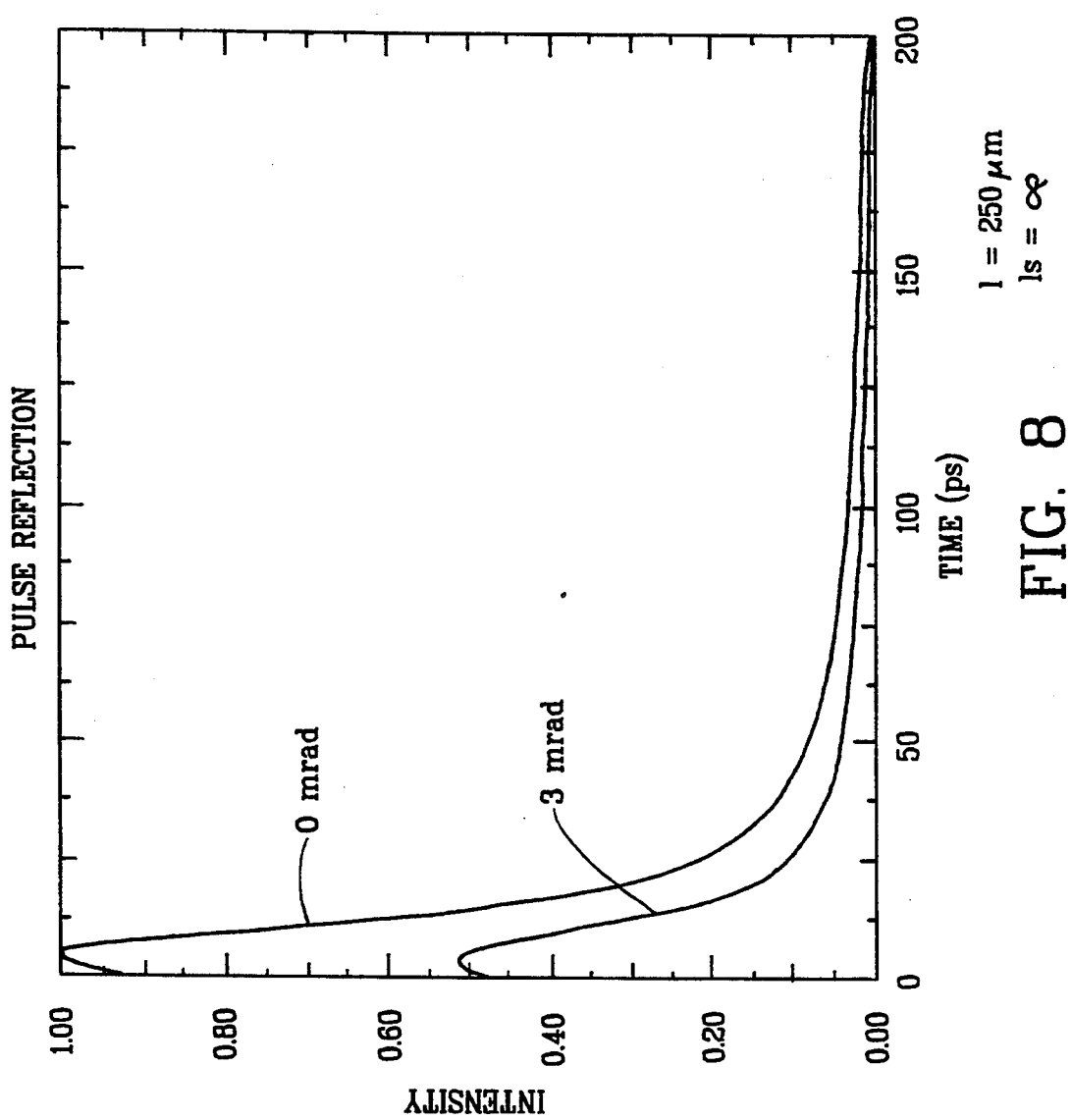
FIG. 8 is a graph showing the theoretical computed scattered pulse profile at two angles, 0 and 3 mrad, respectively, from a nonabsorbing medium with $l=250$ μm.
Figure 9:
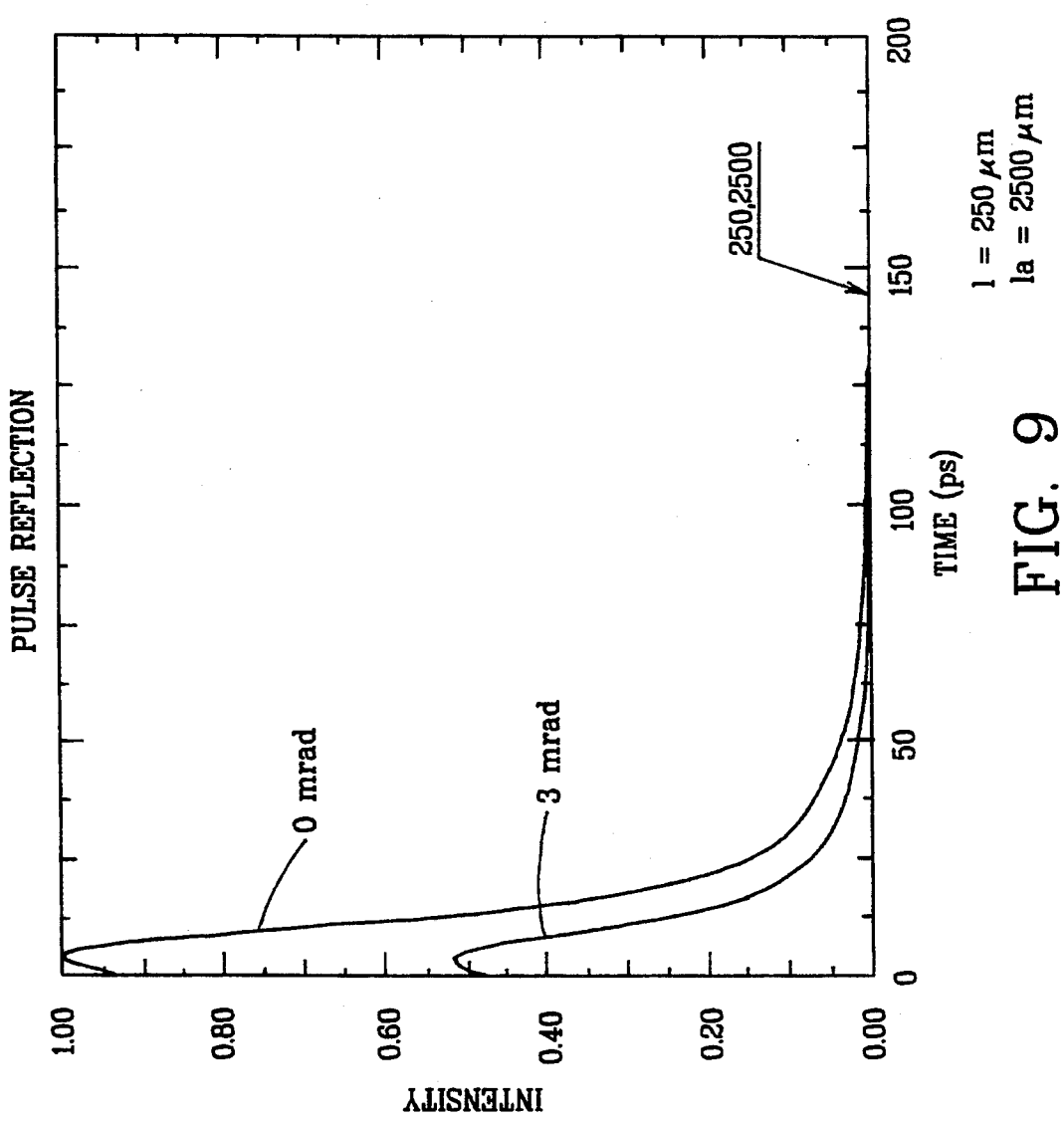
FIG. 9 is a graph showing the theoretical computed scattered pulse profile at two angles, 0 and 3 mrad, respectively, from an absorbing medium with $l=250$ μm and $la=2500$ μm.
Figure 10:
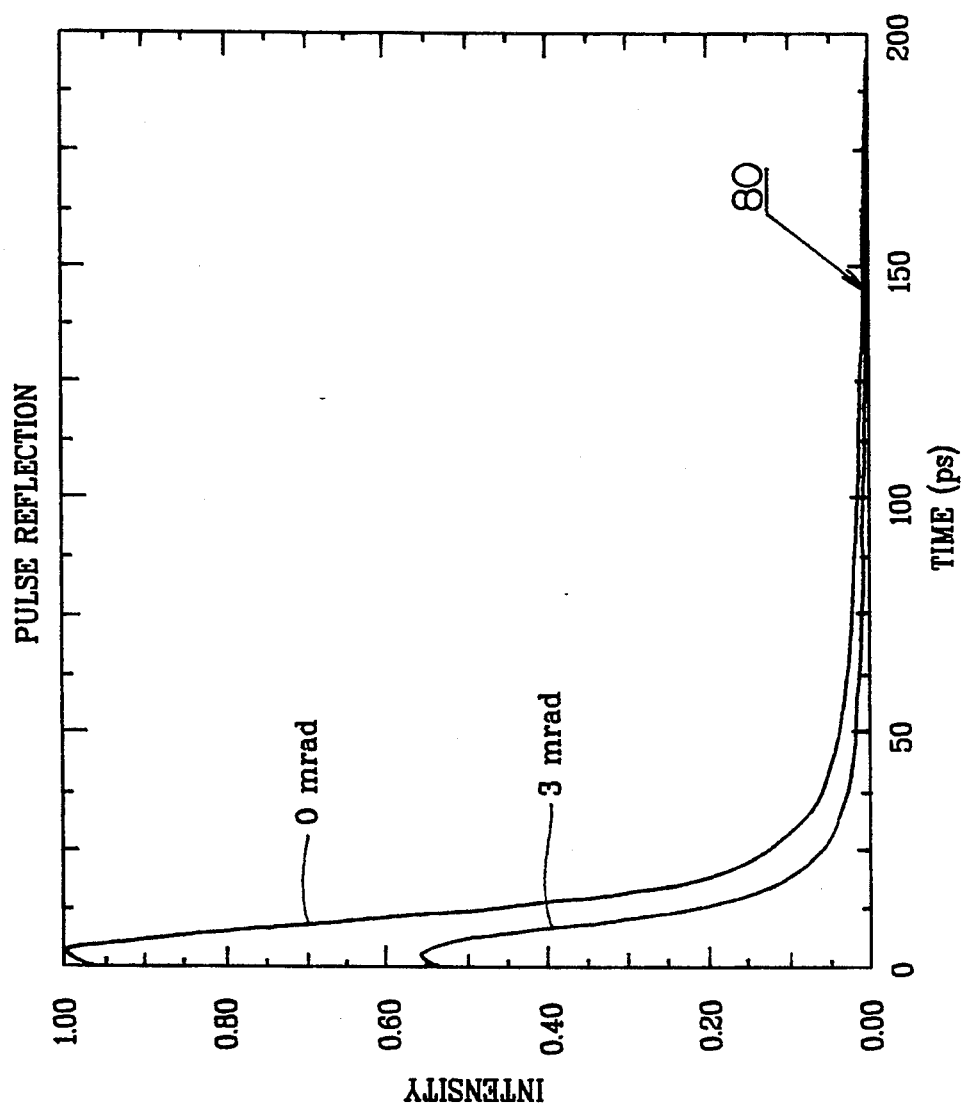
FIG. 10 is a graph showing the theoretical computed scattered pulse profile at two angles, 0 and 3 mrad, respectively, from a nonabsorbing medium with $l=80$ μm.

The intensity of the scattered light in the direction are computed numerically from equation (7). The response function of the instrument is approximated by a Gaussian function with FWHM of 10 ps. FIG. 8 shows the theoretical plots of the scattered pulses at two different angles (0 and 3 mrad) in the backward direction from a nonabsorbing random medium with a transport mean free path of 250 um. The scattered intensity at 0 mrad is always higher than that at 3 mrad because of the coherent interference. FIG. 9 shows a similar plot but with an absorption length of 2500 um. These plots shows a similar plot but with an absorption length of 2500 um. These plots for absorbing medium show that the scattered intensity at later times is reduced because of absorption. The scattered pulses from a medium with shorter transport mean free path of 80 um are plot in FIG. 10. These scattered pulses are narrower compared with those scattered from media with longer mean free path (shown in FIG. 8). The theoretical plots show similar salient features observed in the experiments shown in FIGS. 5 and 6, such as, the scattered light at later time is cut off by absorption, the intensity of light scattered at 0 mrad is higher than those at larger angles, and the pulse profile is broader for light scattered from medium with longer mean free path. However, there are two differences. The two curves at 0 and 3 mrad merge at later times in the case of the experimental results. This can be accounted by the fact that the coherent peak narrows at the light scattered through longer pathlength in the media (come out at late time) and the resolution of the streak camera (0.4 mrad), the enhance intensity at 0 mrad smear out and become negligible when the coherent peak is narrower than said 0.2 mrad.

Figure 11:
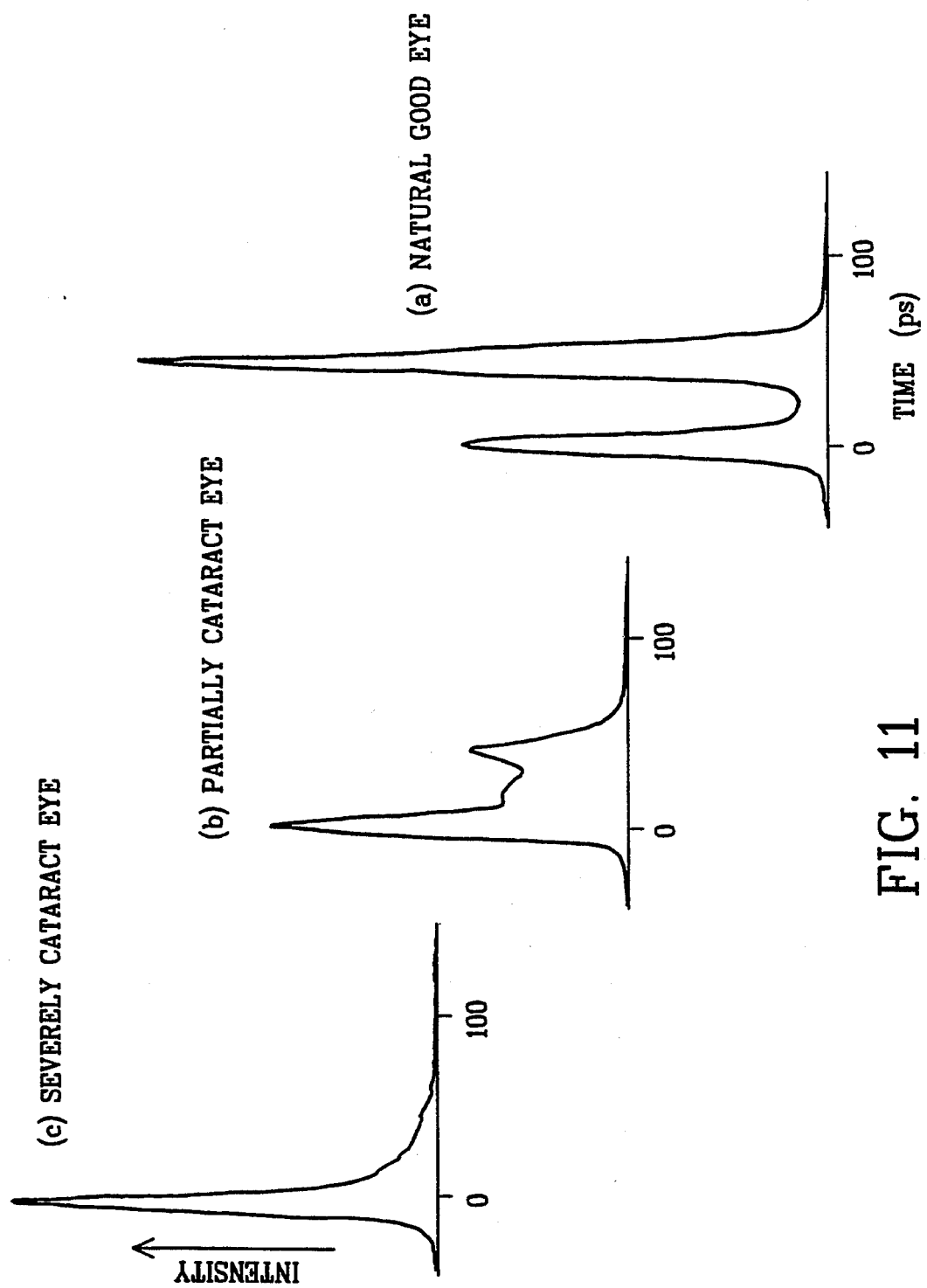
FIG. 11 shows the temporal profiles of an ultrafast laser pulse backscatter from a lens of an eye of a cow having no cataract (curve (a)), having a partial cataract (curve (b)) and having a severe cataract (curve (c)).

Referring now to FIG. 11 there is shown the temporal profiles of an ultrafast laser pulse backscatter from a lens of an eye of a cow having no cataract (curve (a)), a partial cataract (curve (b)) and a severe cataract (curve (c)), the degree of cataract was laboratory generated using hydrogen peroxide solution. The difference in the three curves is clearly evident.

Figure 12:
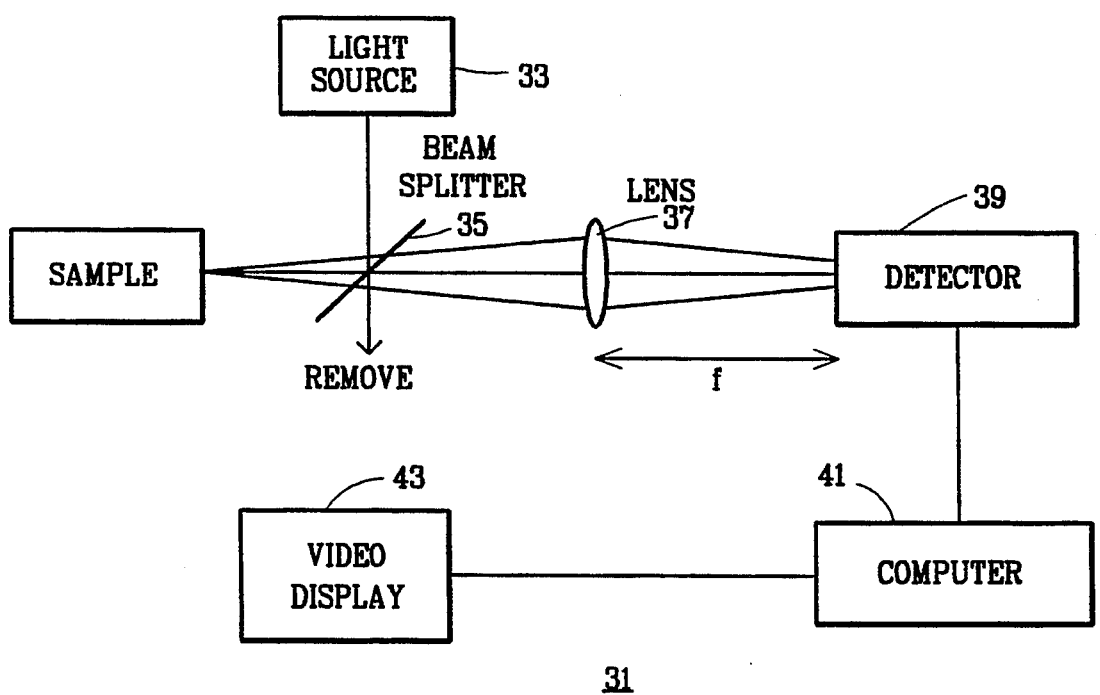
FIG. 12 is a schematic of a system according to this invention for determining l and la by measuring the line shape of the coherent peak.

Referring now to FIG. 12 there is shown an embodiment of a system for determining l and la of a sample S of tissue by measuring the line shape of the coherent peak, the system being identified by reference numeral 31.

System 31 includes a light source 33, a beamsplitter 35, a lens 37, a detector 39, a computer 41 and a video display 43.

Light source 33 is any device or system for producing a collimated beam of light and may comprise for example a continuous wave or a pulse laser or may comprise a lamp, such as a mercury or tungsten-halogen lamp in combination with a collimating lens. Detector 37 may be, for example, video camera or an array of photodiodes or a multiplexor in combination with a phototube.

In the operation of system 31, a collimated beam of light from source 33 strikes beamsplitter 35. The beam reflected off beamsplitter 35 strikes the sample S at an angle of incidence which is greater than 0 degrees, and preferably around 3 or 4 degrees. At least some of the light scattered in the backward direction from sample S passes through beamsplitter 35. Lens 37 collects the light passing through beamsplitter 35 over a preselected angular region, such as for example 3 milliradians and directs the light onto detector 39. The output of detector 39 is fed into computer 41 where it is processed to determine the line shape of the coherent peak and then using the equations listed above to determine l and la. The results are then displayed on video display 43. If desired, the curve corresponding to the line shape of the coherent peak can (also) be displayed on video display 43 or the results of comparing the curve with a curve of a tissue whose condition is known.

As described above, the light collected by lens 37 is the light scattered directly backward about the angle of incidence. This type of scattered light is commonly referred to as backscattered light. At this angle of equals zero the scattered light is coherent and accordingly can be used as imaging signal to obtain information inside a random media. If desired, however, the light collected by lens 37 can be light scattered in the backward direction at any angle and not merely on light scattered back about the angle of incidence. For example the angle of incidence can be 5 degrees and the light collected be at 3 degrees 4 milliradians.

Figure 13:
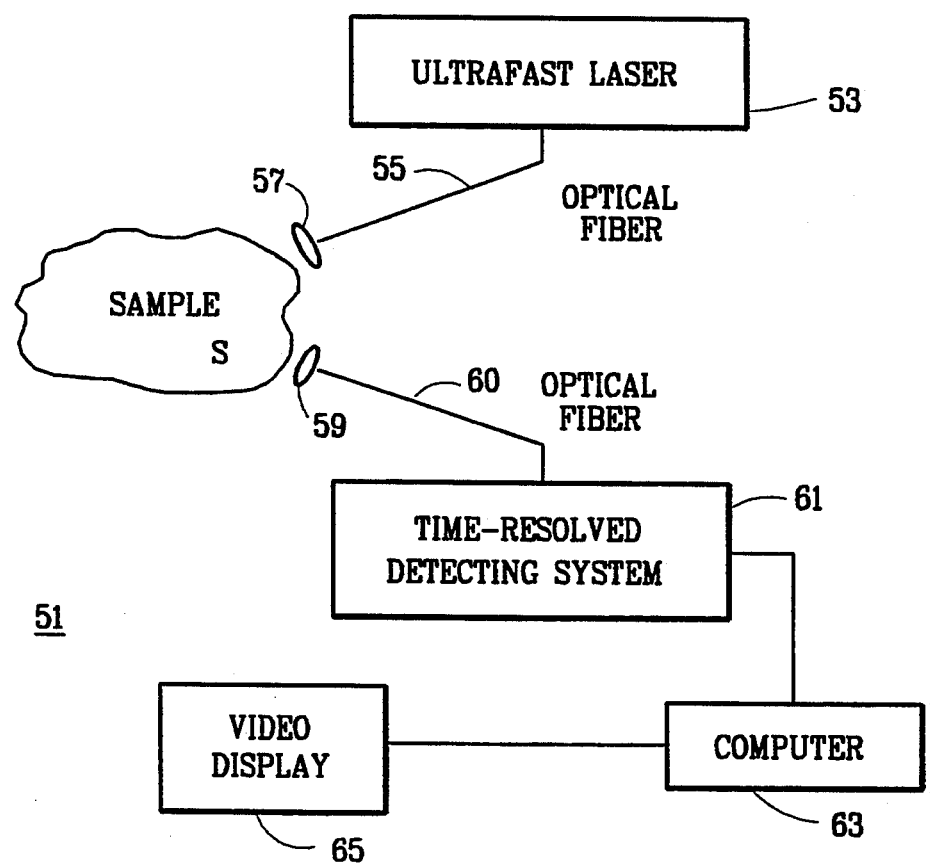
FIG. 13 is a schematic of a system according to this invention for determining l and la by measuring the temporal profile of the scattered pulse.

Referring now to FIG. 13, there is shown an embodiment of a system for determining l and la of a sample S of tissue by measuring the temporal profile of the scattered pulse, the system being identified by reference numeral 51.

System 51 includes a source 53 of ultrafast laser pulses. Pulses from source 53 are passed through an optical fiber bundle 55 collimated by a lens 57 and then strike the sample S. Scattered light emerging from sample S is collected by a lens 59 and carried by an optical fiber bundle 60 to a time-resolved detecting system 61. The output of system 61 is fed into a computer 63 where the information is processed. The results are then displayed on a display 65.

Source 53 may be a high repetition rate mode locked laser such as a semiconductor diode laser or a mode locked dye laser or a YAG laser or a tunable solid state laser. Lens 59 is positioned relative to lens 57 so as to collect scattered but not reflected light. The scattered light is not limited to light scattered in the backward direction. In the schematic, the angle of incidence is about +10 degrees from normal and lens 59 is positioned at an angle D of about −10 from the normal. Detecting system 61 may comprise a streak camera whose output is coupled to a video camera or a microchannel plate photomultiplier tube coupled to a sampling oscilloscope. And la are determined in computer 63 using the equations listed above. Display 65 can either display l and la and/or the temporal profile and/or the results of comparing l and la and the temporal profile with normal curves and/or values.

Figure 14:
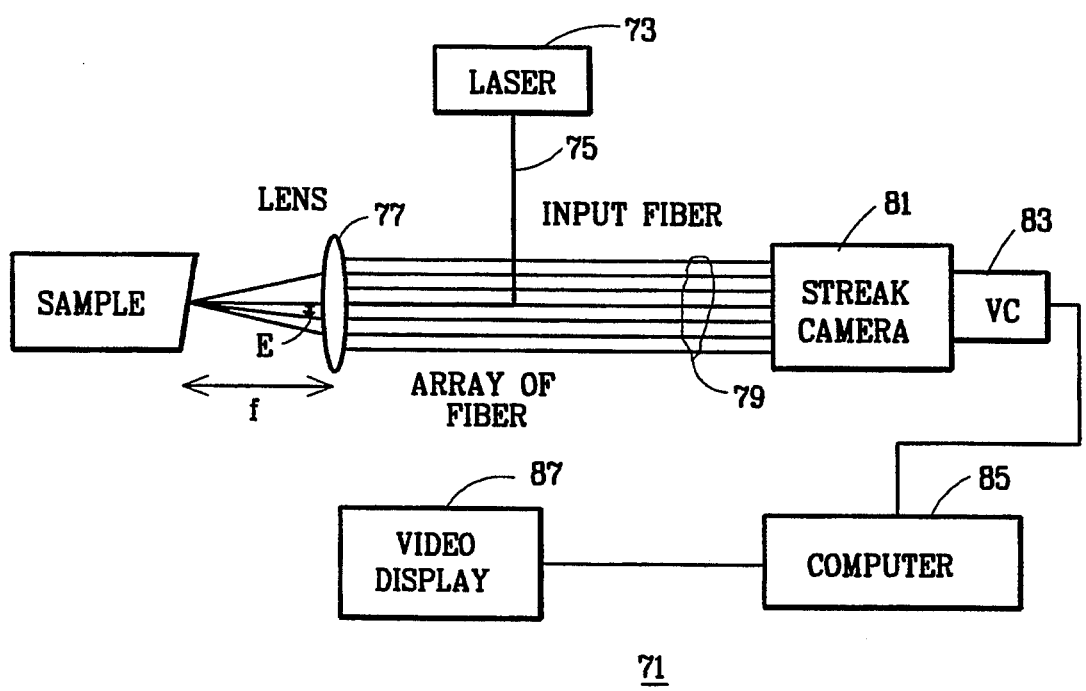
FIG. 14 is a schematic of a system according to this invention for determining l and la by measuring the line shape of the coherent peak and/or the temporal profile of the scattered pulse.

Referring now to FIG. 14, there is shown an embodiment of a system for either angularly resolving or temporally resolving a scattered pulse and then determining l and la from the information so obtained, the system being identified by reference numeral 71.

Light pulses from high repetition rate mode locked laser 73 is transmitted through an optical bundle 75, collimated by a lens 77 and then strikes sample S at an angle E of 6 degrees from the normal. Light scattered in the backward direction is collected by lens 77 and then passed through an array of fibers 79 to the input slit of a streak camera 81 whose output is coupled to a video camera 83. The output of video camera 83 is connected to a computer 85. The information obtained in computer 85 is displayed on video display 87.

The scattered pulse can be angularly resolved by operating streak camera 81 in the focus mode and can be temporally resolved by operating streak camera 81 in the streak mode.

Figure 15A:
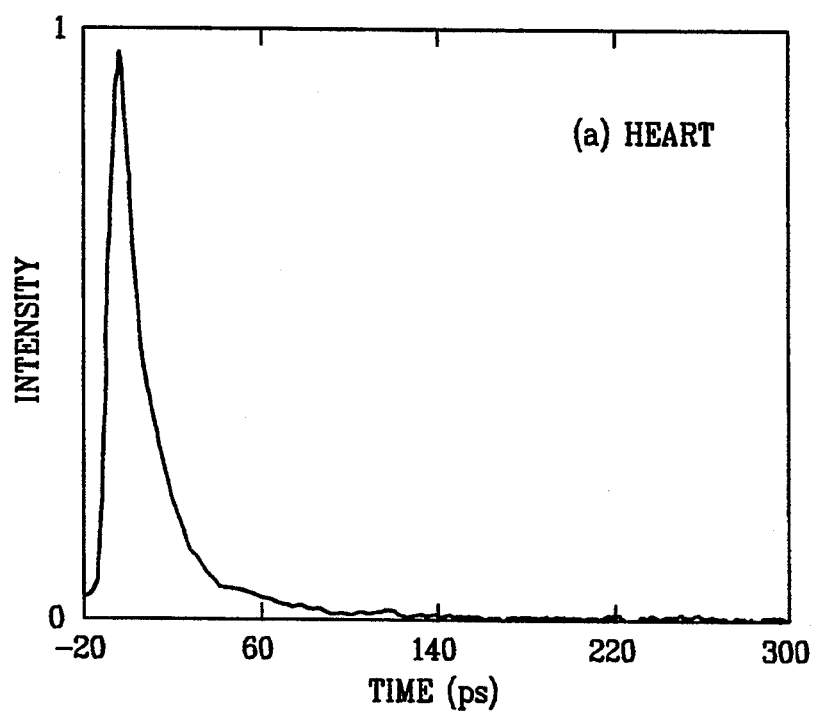
FIG. 15(a) and 15(b) are graphs showing temporal profiles of the backscattered pulse from the non-fat and fat portion, respectively of a chicken heart.
Figure 15B:
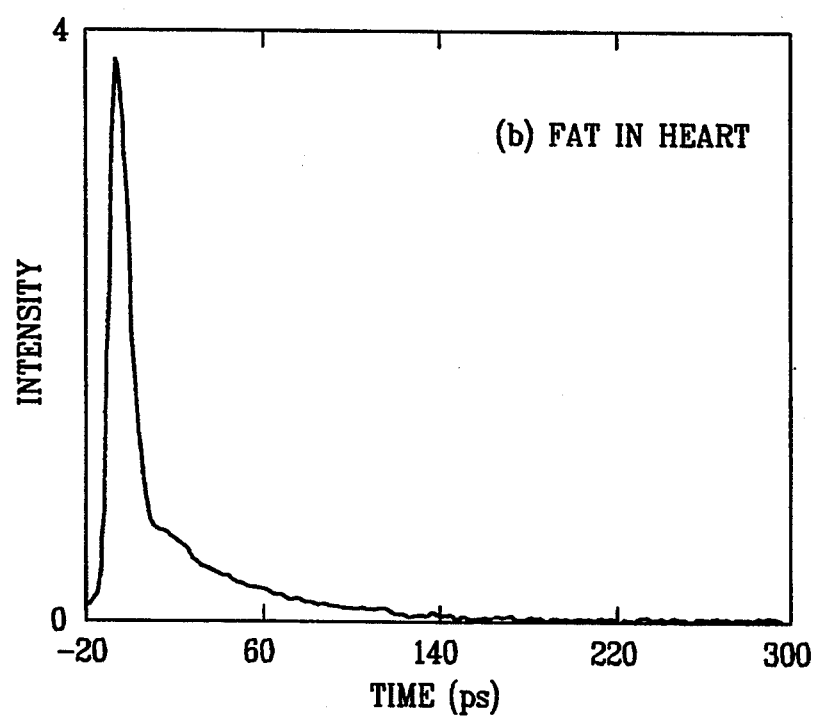

Referring now to FIGS. 15(a) and 15(b) there is shown a graph of the temporal profiles of the backscattered pulse from the non-fat and fat portion, respectively, of a heart. As can be seen, the curve for the fat portion is narrower than the curve for the non-fat (or normal) portion. Thus, there is a difference in and a for normal (non fat) and abnormal cardio-vascular system.

Figure 16:
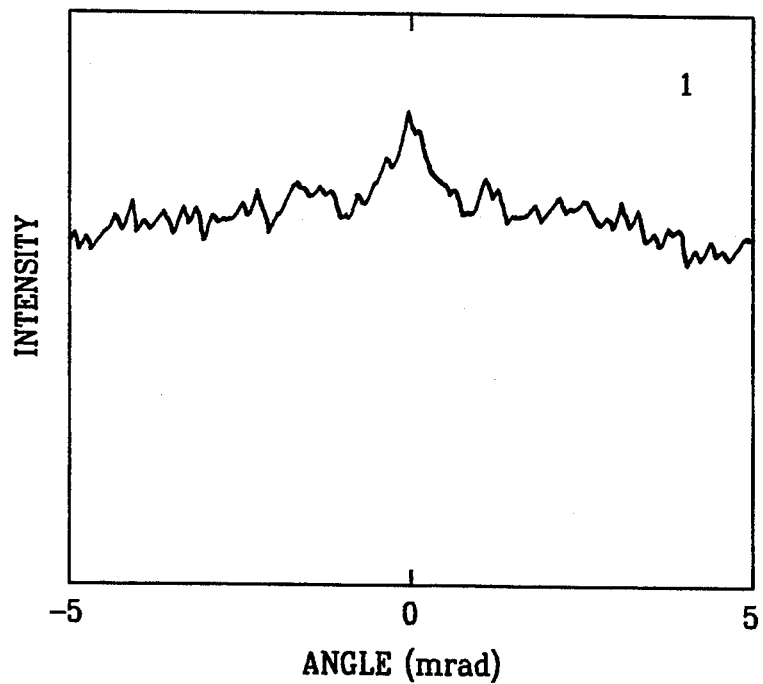
FIG. 16 is a graph of the angular distribution of the intensity of light backscattered from a bone tissue i.e. a human tooth.
Figure 17:
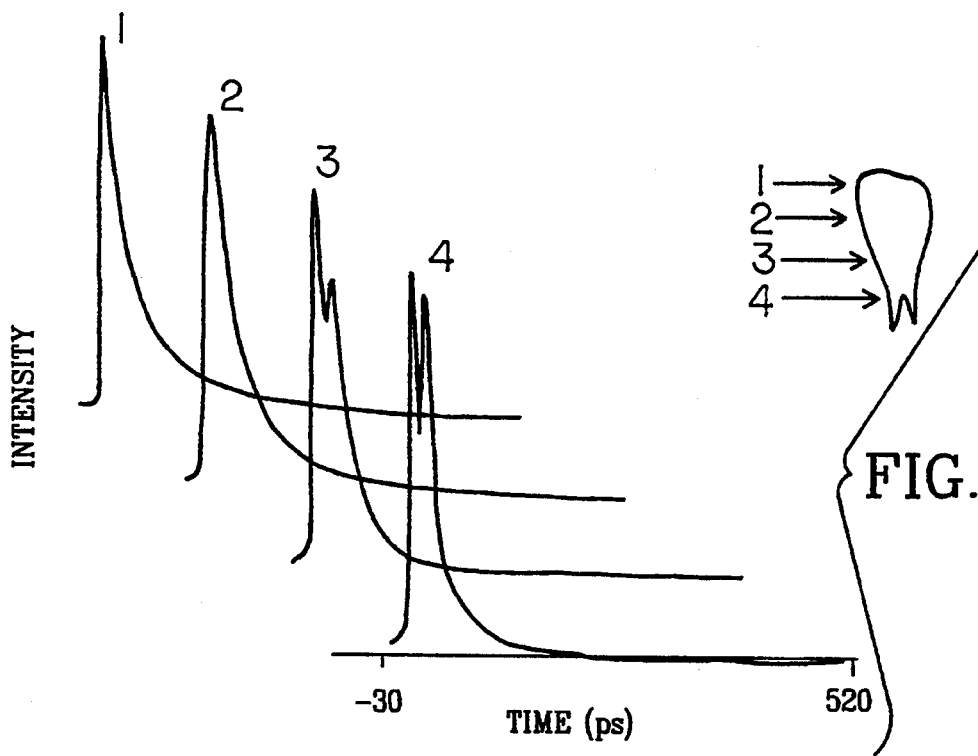
FIG. 17 are graphs showing temporal profiles of the backscattered pulse from four different sections of the tooth referred to in FIG. 16.

The intensity of backscatter in time and angle for bone i.e. a tooth are displayed in FIGS. 16 and 17. The temporal and angular profiles, respectively show that the properties of quality of bone can be analyzed using l and la. The double peak indicates a cavity on the tooth.

Figure 18:
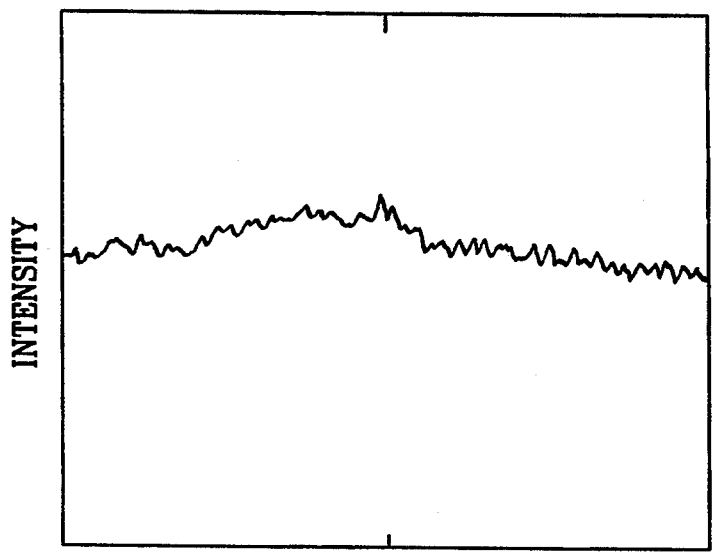
FIG. 18(a) and 18(b) is a graph showing the angular distribution of the intensity of light backscattered from a plant leaf with and without chlorophyll, respectively.
Figure 18:
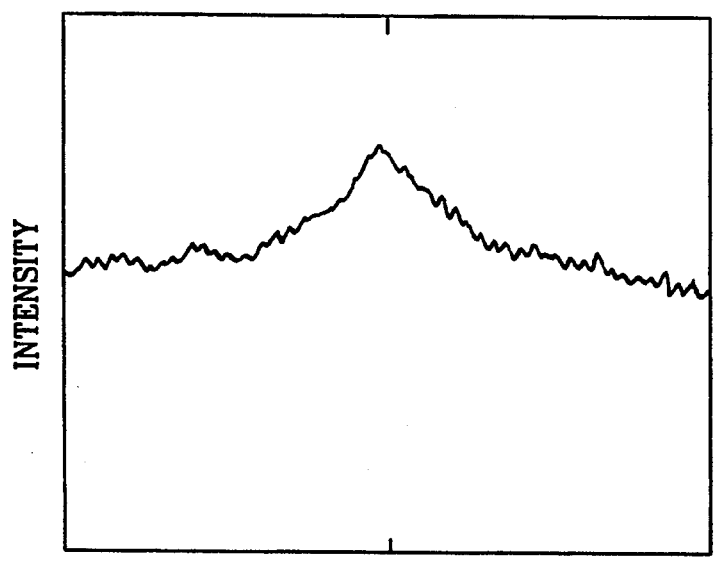

The angular distribution of the intensity of light backscattered from a plant leaf with chlorophyl and without chlorophyl is shown in FIGS. 18(a) and 18(b), respectively.

The embodiments of the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. Noninvasive apparatus for characterizing biological material comprising:
   a. a laser for illuminating the biological material with a beam of light,
   b. means for measuring the intensity of light scattered from the biological material in the backward direction over a predetermined angular region as a result of illumination by said laser,
   c. a computer coupled to said detecting means for analyzing the scattered light as detected to determine the absorption length ($l_a$) and the transport mean free path (1) and then comparing the results so obtained to reference values stored in said computer, and
   d. means coupled to said computer for displaying the results of the comparison made by the computer.

2. Noninvasive apparatus for characterizing biological material comprising:
   a. a laser for producing a pulse of light,
   b. a lens for directing said pulse of light from said laser onto said biological material, and collecting light scattered from the biological material in the backward direction,
   c. a streak camera constructed for either angularly or temporally resolving the light collected by the lens,
   d. a video camera coupled to the output of the streak camera,
   e. a computer coupled to the output of the video camera for processing the output of the video camera to determine the absorption length ($l_g$) and the transport mean free path (1) from the output of the video camera so obtained and comparing the results obtained to reference values stored in said computer, and
   f. a display for displaying the results from the computer.

3. A noninvasive method of characterizing biological material comprising:
   a. illuminating the biological material with a beam of light,
   b. measuring the intensity of the light scattered from the biological material in the backward direction over a predetermined angular region, the measurements so obtained corresponding to the angular line shape of the coherent peak of the scattered light, and then
   c. determining the condition of the biological material using said measurements.

4. The method of claim 3 and wherein determining the condition of the biological material comprises comparing the angular line shape of the coherent peak so obtained with the angular line shape of the coherent peak of a sample of the same type of biological material whose condition is known.

5. The method of claim 3 and wherein determining the condition of the biological material comprises determining the absorption length and the transport mean free path from the angular line shape of the coherent peak and then comparing the absorption length and the transport mean free path so obtained with known values.

6. The method of claim 3, wherein said biological material is from the heart, breast, cervix, vagina, skin, vascular system, eye, bone or lung of a human or animal or from a plant leaf.

7. The method of claim 3 and wherein determining comprises determining the absorption length ($1a$) and the transport mean free path (1) from the intensity measurements so obtained.

8. A noninvasive method of characterizing biological material comprising:
   a. illuminating the biological material with a beam of light,
   b. measuring the intensity of the light scattered from the biological material in the backward direction as a function of time, the measurements so obtained corresponding to the temporal profile of light scattered in the backward direction, and then c. determining the condition of the biological material using said measurements, said determining comprising determining the absorption length and the transport mean free path from the intensity measurements of the temporal profile so obtained.

9. The method of claim 8, wherein said biological material is from the heart, breast, cervix, vagina, skin, vascular system, eye, bone or lung of a human or animal or from a plant leaf.

10. The method of claim 8 and wherein the intensity measurements correspond to the temporal profile of light scattered in the backward direction over an angular region of 0 mrad.

11. The method of claim 8 and wherein the intensity measurements correspond to the temporal profile of light scattered in the backward direction over an angular region of greater than 0 mrad.

* * * * *